United States Patent
Swain et al.

(10) Patent No.: US 6,936,290 B2
(45) Date of Patent: *Aug. 30, 2005

(54) ENZYME TREATED MAPLE SYRUP AND SHELF STABLE PRODUCTS CONTAINING ENZYME TREATED MAPLE SYRUP

(75) Inventors: Robert Swain, Toronto (CA); Stephan Jampen, Guelph (CA)

(73) Assignee: Shady Maple Farm Ltd., Mississauga (CA)

( * ) Notice: Subject to any disclaimer, the term of this patent is extended or adjusted under 35 U.S.C. 154(b) by 250 days.

This patent is subject to a terminal disclaimer.

(21) Appl. No.: 10/146,811

(22) Filed: May 17, 2002

(65) Prior Publication Data

US 2002/0197351 A1 Dec. 26, 2002

Related U.S. Application Data

(63) Continuation-in-part of application No. 09/858,602, filed on May 17, 2001, now Pat. No. 6,485,763.

(51) Int. Cl.$^7$ .............................. C13F 3/00; A23L 1/09
(52) U.S. Cl. ............................ 426/48; 426/52; 426/638
(58) Field of Search .......................... 426/48, 52, 322, 426/638, 589, 658, 655

(56) References Cited

U.S. PATENT DOCUMENTS

| | | | |
|---|---|---|---|
| 3,615,701 A | 10/1971 | Goss | 99/142 |
| 3,878,306 A | 4/1975 | Garstick | 426/658 |
| 4,006,032 A | 2/1977 | Hills | 127/46 A |
| 4,159,210 A | 6/1979 | Chen et al. | 127/29 |
| 4,226,895 A | 10/1980 | Miller et al. | |
| 4,938,989 A | 7/1990 | Steeves et al. | 426/658 |
| 5,049,199 A | 9/1991 | Capen | 127/9 |
| 5,389,209 A | 2/1995 | Paquette | 203/14 |
| 5,529,800 A | 6/1996 | Bourns et al. | |
| 5,876,506 A | 3/1999 | Cherukuri et al. | 127/63 |
| 6,485,763 B1 | 11/2002 | Jampen | |

FOREIGN PATENT DOCUMENTS

| | | |
|---|---|---|
| WO | WO-WO 97/36501 A1 | 10/1997 |
| WO | WO-WO 00/53024 A1 | 9/2000 |
| WO | WO-WO 01/97632 A1 | 12/2001 |
| WO | WO-WO 02/091854 A2 | 11/2002 |

OTHER PUBLICATIONS

Jeffery, M.S., Key Functional Properties of Sucrose in Chocolate and Sugar Confectionery, Food Technology, 47(1): 141–144 (XP000338473) (1993).

H.A. Edson, et al., Vermont Agricultural Experiment Station, Bulletin No. 167, University of Vermont and State Agricultural College, Burlington, VT, Jun. 1912, pp. 324–605.

The Ohio State University Bulletin, North American Maple Syrup Producers Manual, Bulletin 856, Chapter 7—Maple Syrup Production, Increasing Evaporation Efficiency, through Chapter 9—Other Maple Products, Dec. 1998.

The Ohio State University Bulletin, North American Maple Syrup Producers Manual, Bulletin 856, Appendix 2—Maple Chemistry and Quality, Dec. 1998.

J.F. Steffe, Rheological Methods in Food Process Engineering, second edition, Freeman Press, East Lansing, MI, pp. 26, 82 and 367, 1996.

AOAC Official Method 977.20, Separation of Sugars in Honey, Liquid Chromatographic Method, 1998.

Hayward, et al., Some Factors Causing Dark–Colored Maple Sirup, New York State Agricultural Experiment Station, Bulletin No. 718, Mar. 1946.

Woodward, et al., "Enzymatic Conversion of Sucrose to Hydrogen", Biotech. Prog., 14(6): 897–902, Nov. 1998.

AOAC Official Method 932.14 Solids in Sirups, Official Methods of Association of Official Analytical Chemists (AOAC) International, 16$^{th}$ Edition, 4$^{th}$ Revision, 1998.

The Ohio State University Bulletin, North American Maple Syrup Producers Manual, Bulletin 856, Chapter 9—Other Maple Products– Some Common Maple Products, Maple Spread (maple cream, maple butter) at http://ohioline.osu.edu/b856/b856_105.html (Oct. 27, 2004).

Primary Examiner—Keith Hendricks
(74) Attorney, Agent, or Firm—Covington & Burling

(57) ABSTRACT

A method for producing a shelf stable, high viscosity maple syrup product is provided, which comprises adding a sucrose-cleaving enzyme to maple syrup and incubating the resulting solution. Also provided is a shelf stable, spreadable maple syrup product with a consistency similar to that of clear honey, which may be used as a spread, or sweetener or a topping. Also provided is a shelf stable maple butter product, with the consistency of churned honey, which may be used as a spread, sweetener, topping, or snack. Both the spreadable maple syrup product with the consistency of clear honey and the spreadable maple butter with the consistency of churned honey are also suitable for use in pure maple-based products or other foods.

43 Claims, 2 Drawing Sheets

ENZYME TREATED MAPLE SYRUP AND SHELF STABLE PRODUCTS CONTAINING ENZYME TREATED MAPLE SYRUP

CROSS REFERENCE TO RELATED APPLICATIONS

The application is a continuation-in-part of U.S. patent aplication Ser. No. 09/858,602 filed May 17, 2001, now U.S. Pat. No. 6,485,763, which is incorporated by reference in its entirety.

FIELD OF THE INVENTION

The present invention relates to (1) a spreadable, shelf stable maple syrup product with the consistency of clear honey, (2) an enzyme treated maple syrup that when added to a product increases the shelf stability of the product by preventing the visible crystallization or separation of the product, and (3) a shelf stable maple based product, for example spreadable, shelf stable maple butter with the consistency of churned honey.

BACKGROUND OF THE INVENTION

The sap of maple trees forms the basis of maple-based products, including maple syrup, maple sugar and maple confection products. Maple syrup is obtained by the concentration of maple sap, a low solids (low sugar) solution obtained from the maple tree, to a solids content of 66 percent (66 degrees Brix). The production of maple syrup and related products is highly regulated in Canada and the United States, such that all additives are prohibited. As a result, maple producers cannot simply use additives such as stabilizers if they wish to label their product as a "pure maple-based product" or as " pure maple syrup".

To produce maple syrup, the sap from maple tree is concentrated to 66 degrees Brix (at 68 degrees Fahrenheit; 20 degrees Celsius) to be considered as "pure maple syrup" by U.S. and Canadian law. About 40 liters of maple sap are needed to make 1 liter of maple syrup. During the evaporation process, the sap is heated which induces chemical changes that give maple syrup its characteristic color and flavor. These chemical changes include non-enzymatic browning and caramelization reactions (Edson, 1910; Hayward and Pederson, 1946).

Concentration can be achieved through simple boiling in an open kettle or using more advanced evaporation techniques such as vacuum pan evaporators and rising film or falling film evaporators. Various other methods are known for concentrating maple sap. For example, U.S. Pat. No. 5,389,209 to Paquette discloses a method of boiling the sap under normal pressure, then heating the sap to below boiling temperature and using an air circulating column to further evaporate the water. Reverse osmosis can be used to preconcentrate the sap to about 20–25 degrees Brix. An alternate concentration step, which involves the addition of heat, must be used to complete the concentration to 66 degrees Brix such that the characteristic maple flavor is created (North American Maple Producers Manual, Bulletin 856, chapter 7).

Concentrating to a higher level (over 67.5 degrees Brix) will result in crystallization of the sucrose, the main sugar found in maple sap, within the container while in storage. Conversely, a maple syrup of lower Brix (under 64.5 degrees Brix) would spoil (ferment) while in storage. Crystallization occurs because the main sugar in maple syrup is sucrose (90–100 percent), with the rest being glucose (0 to 10 percent) (North American Maple Syrup Producers Manual, Bulletin 856, Appendix 2).

It is the crystallization behavior of maple syrup at higher concentration that allows for the production of other maple-based products such as maple sugar. These products are obtained by concentrating maple syrup past 66 degrees Brix. At these elevated Brix levels, a supersaturated sucrose solution is made. Therefore, if this solution is cooled, crystallization will occur. Depending on the rate of cooling and/or whether agitation is present during the cooling process, characteristic maple-based products are obtained. Slow cooling without agitation results in crystals that are very large, often termed "rock candy". More rapid cooling, but again without agitation, will result in smaller crystals but the product has a very gritty mouthfeel. When a highly supersaturated maple syrup solution (85 to 90 degrees Brix) is cooled very rapidly without agitation, a non-crystalline glass-like solid is obtained (North American Maple Syrup Producers Manual, Bulletin 856, chapter 9).

Conversely, if a supersaturated (84 to 85 degrees Brix; or 12 to 13 degrees Celsius above the boiling point of water) maple syrup solution is cooled rapidly with high-speed agitation, very small crystals are obtained with the resultant product being paste-like in consistency and is spreadable. This product is known as maple butter or maple cream. Currently there is no pure maple-based product with this paste-like consistency that is shelf stable.

Crystallization of the sugars found in maple syrup is random and occurs spontaneously at higher Brix levels. Because the crystallization behavior of concentrated maple sap is difficult to control, only a select few products have been developed. Additionally, at a concentration of 66 degrees Brix, maple syrup may be too runny (thin) to be used in an application such as a honey like spread. Currently, there is no natural or pure maple-based product which has the consistency and/or appearance similar to that of clear honey.

Clear honey is a transparent high viscosity 3.9 Pascal seconds sugar syrup with a moisture content of 17 to 19 percent (81 to 83 degrees Brix solids) (Rheological Methods in Food Process Engineering, Steffe, J. F. 1996, pp 82, 26 and 367). This material remains in a clear state, without crystallization for extended periods of time. The main sugar components in honey are the monosaccharides glucose and fructose. These sugars are present in maple syrup in small amounts.

As previously described, a more viscous solution similar to that of clear honey, having a unique maple flavor, is attainable by further concentrating maple syrup to a higher Brix level (81 to 82 degrees Brix for example). However, when this supersaturated solution is cooled, crystallization occurs rapidly such that the clear viscous solution would not be preserved. This occurs because the main sugar in maple syrup is the disaccharide sucrose, which crystallizes much more readily than glucose and fructose.

Pure glucose and fructose blends are available commercially and are known as invert sugars. It is known to use invert sugar (glucose/fructose) when making artificial maple-based products. It is also known that invert sugar tends to retard crystallization in maple-based products. However, simply adding invert sugar can lead to loss of natural maple flavor. Additionally, the resultant maple-based product may no longer be labeled or considered as pure under the Canadian and U.S. legal standards.

Invert sugars have also been used in making imitation maple syrup or syrup substitutes. U.S. Pat. No. 3,878,306 to Garstick discloses an imitation maple syrup made from various sugars and artificial flavorings. U.S. Pat. No. 4,938,989 to Steeves and McKelvey provides a maple syrup substitute which contains maple syrup, maple flavor, fructose and glucose and white sugar. Again, these products could not be considered pure maple-based products.

It is known in the art that sucrose can be cleaved into its constituent sugars, glucose and fructose by use of an acid such as L-tartaric acid (cream of tartar). However, the use of organic acids leads to products that have very poor flavor profiles and unacceptable appearances. A further challenge is that the acid would have to be removed, after it has cleaved the sucrose. This step would also remove important flavor components.

The difficulty in making stable high viscosity maple syrups extends to other maple-based products. For example, maple butter (also called maple cream or maple spread) separates into two layers if not stored at temperatures below 0 degrees Celsius or 32 degrees Fahrenheit. A dilute syrup layer forms on top and a solid crystalline mass forms underneath. Maple butter is made by heating maple syrup to 11 to 13 degrees Celsius above the boiling point of water (83 to 86 degrees Brix), and cooling rapidly while stirring.

Many viscosity-altering hydrocolloid substances are commonly used in food products, and are known in the art as stabilizing products, or 'stabilizers'. Two commonly used stabilizers are carageenan and xanthan. Stabilizers are added to prevent phase separation in liquids or solids such as ice cream and peanut butter. However, these stabilizers have not been used to date in maple-based products. Carrageenan is extracted from seaweed, while xanthan is derived from an industrial fermentation of a bacteria.

Accordingly, there is a need for a shelf stable, spreadable, non-crystalline maple syrup product with the consistency of clear honey.

Accordingly, there is also a need for an enzyme treated maple syrup that when added to products increases the shelf stability of the product by preventing the visible crystallization or separation of the product. There is also a need for shelf stable products containing enzyme treated maple syrup.

Accordingly, there is also a need for a spreadable, shelf stable, maple butter with the consistency of churned honey.

Accordingly, there is also a need for a shelf stable, maple butter that is a pure maple-based product.

SUMMARY OF THE INVENTION

As used herein, the term maple syrup refers to concentrated or unconcentrated sap of the botanical genus *Acer*. It is in the scope of this invention that the unconcentrated maple sap may be used directly.

There are three objects of the present invention: (1) to provide a shelf stable, spreadable, non-crystalline maple syrup product with a consistency similar to that of clear honey, wherein the product is preferably transparent or translucent, (2) to provide a shelf stable maple-based product with high Brix value, for example, shelf stable maple butter with a similar consistency to churned honey, and (3) to provide an enzyme treated maple syrup product which is a pure maple syrup product, which when added to other products increases the shelf stability of the products by preventing the visible crystallization or separation of the products. The enzyme treatment cleaves the main sugar in maple syrup (sucrose) to yield glucose and fructose. Products containing a high concentration of sucrose are not shelf stable and will crystallize, whereas products containing a similarly high concentration of the combination of glucose and fructose, and proportionally less sucrose will not crystallize or separate as readily.

An object of the present invention is to provide a spreadable, shelf stable maple syrup product having a Brix measurement of between about 72 and about 90 degrees Brix. Preferably, the Brix measurement is between about 77 and about 87 degrees, with the most preferred range being between about 83 to about 86 degrees.

Another object of the invention is to provide a method for producing a shelf stable maple syrup composition with a consistency similar to that of clear honey comprising treating maple syrup with a sucrose-cleaving enzyme. Preferably, the sucrose-cleaving enzyme is invertase. Preferably, the method includes the additional step of concentration of the maple syrup to between about 72 and about 90 degrees Brix.

According to an aspect of the invention there is provided a method for producing a stable high viscosity maple syrup product comprising adding a sucrose cleaving enzyme to maple syrup and incubating the resulting maple syrup solution.

According to another aspect of the invention there is provided a shelf stable, spreadable maple syrup composition having a Brix measurement of between about 72 and about 90 degrees.

According to a further aspect of the invention there is provided the method of using the shelf stable, spreadable maple syrup composition with a consistency of clear honey as a spread, sweetener or in other food products such as ice cream or other desserts.

Another object of the present invention is to provide a method of producing an enzyme treated maple syrup, that when added to a product increases shelf stability by preventing the visible crystallization or separation of the maple based product, comprising (1) adding a sucrose-cleaving enzyme, for example, invertase, to maple syrup and (2) incubating the maple syrup to produce the enzyme treated maple syrup. Optionally, the method could include the further steps of concentrating the enzyme treated maple syrup and removing the sucrose-cleaving enzyme post-incubation. The method could also include the optional step of diluting the maple syrup to between about 55–66 degrees Brix prior to the addition of the sucrose-cleaving enzyme. Optionally, the product is a maple-based product.

Another object of the present invention is to provide an enzyme treated maple syrup that is a pure maple-based product, and that when added to a product increases the shelf stability of the product by preventing the visible crystallization and separation of the product. The product may be a maple based product, fudge or a condiment.

Another object of the invention is to provide a method for stabilizing a maple-based product comprising, (1) combining the maple-based product with an enzyme treated maple syrup, or one or more stabilizers, or a combination of both to form a stabilized maple-based product, and (2) optionally, concentrating the maple syrup solution. The stabilizer can be any or all of one or more viscosity altering hydrocolloids. Optionally, air or an inert gas, for example nitrogen, can be added after concentrating the solution while cooling. In another object, a method is provided to stabilize a product by combining the product with an enzyme treated maple syrup.

Another object of the invention is to provide a stabilized maple-based product.

Another object of the invention is to provide a method or producing shelf stable maple butter which comprises, (1)

combining maple syrup with an enzyme treated maple syrup, or one or more stabilizers, or a combination of both to form a maple syrup solution, and (2) concentrating the maple syrup solution. The stabilizer can be any or all of one or more viscosity altering hydrocolloids. Optionally, air or an inert gas, for example nitrogen, can be added after concentrating the solution while cooling. Optionally, the viscosity altering hydrocolloid is xanthan or carageenan or both, at a concentration of about 0.1 to 1 percent. Optionally the ratio of pure maple-based product stabilizer to maple syrup is 20:80 to 25:75 by percentage of sugars present. Optionally the resulting maple butter is concentrated to between 83 degrees Brix and 86 degrees Brix.

Another object of the present invention is to provide a method of producing a shelf stable maple butter, comprising: (a) adding a sucrose-cleaving enzyme to a maple syrup; (b) incubating the maple syrup to produce an enzyme treated maple syrup; (c) inactivating or removing the sucrose cleaving enzyme; and (d) concentrating the enzyme treated maple syrup to produce the shelf stable maple butter. Optionally, the sucrose-cleaving enzyme is invertase. Optionally, the maple syrup is diluted to about 55 to 66 degrees Brix prior to the step of adding the sucrose cleaving enzyme. The sucrose-cleaving enzyme may be removed by filtration or inactivated by heat treatment. However, due to requirements of various regulatory agencies, it may be necessary to remove the enzyme in order to meet applicable regulatory standards for pure maple-based products. Further, the method may comprise the additional step of monitoring the ratio of sucrose to fructose and glucose, and removing or inactivating the sucrose cleaving enzyme at a predetermined sucrose to fructose and glucose ratio, followed by the step of concentrating. Also provided is the maple butter produced by this method.

Another object of the invention is to provide the stabilized maple butter, which is shelf stable and can be a pure maple-based product.

Another object of the invention is to provide a method of making a maple-based product with improved flavor, for example maple butter, comprising (1) concentrating maple syrup, and (2) adding air or an inert gas, for example nitrogen, after concentrating, while cooling. Optionally, air can be added during the cooling step. Optionally, the air or the inert gas is added to a final concentration of 1% to 15%, most preferably to a final concentration of 12 percent.

Another object of the invention is to provide the improved flavor maple-based product.

According to a further object of the invention there is provided a method of using a stabilized maple-based product as a spread, sweetener, or a topping, or on its own as a snack food product.

According to a further object of the invention there is provided a method of using a stabilized maple-based product as an ingredient in the manufacture of a pure maple-based product.

DETAILED DESCRIPTION OF THE DRAWINGS

DETAILED DESCRIPTION OF THE INVENTION

Figure 1:
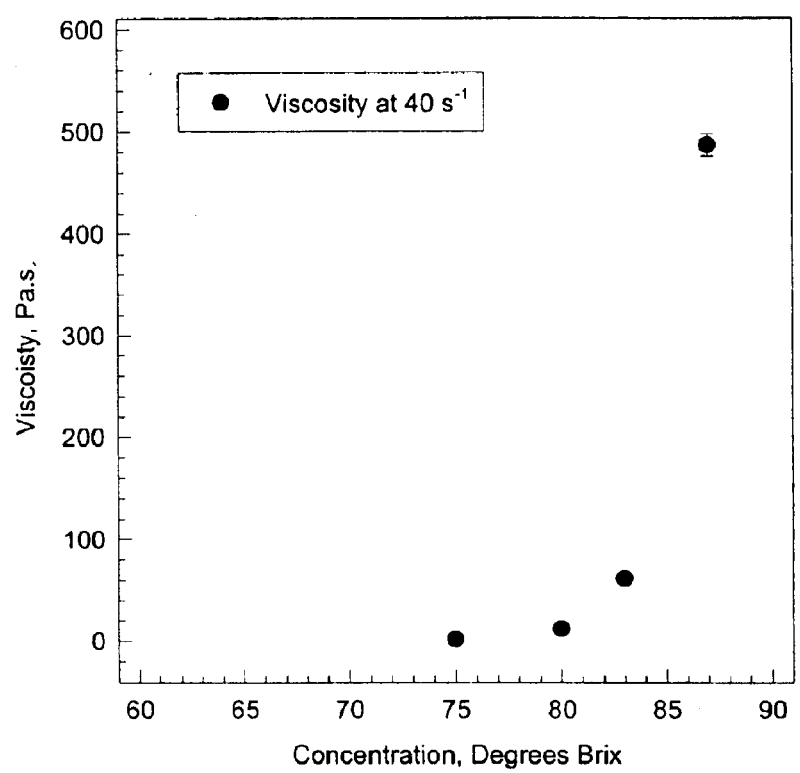
FIG. 1 is a graph showing the viscosity profile of a 55:45 enzyme treated to non-enzyme treated blend of maple syrup at various concentrations at 25° C.

The present invention provides a spreadable maple syrup product which is shelf stable, having a consistency similar to that of clear honey. The maple syrup product may be used in a similar manner as honey: as a topping on bread products, topping for other food products such as ice cream or other desserts, or as a sweetener in home cooking and/or in commercial food products. It is also suitable for use in pure maple-based products.

The present invention also provides an enzyme treated maple syrup that can be used to increase the shelf stability of a variety of maple syrup products or other products, for example, fondants, fudge and other crystalline candy. This enzyme treated maple syrup has the advantage of itself being a pure maple-based product.

The present invention also provides a shelf stable maple butter which is spreadable and paste-like in consistency. The maple butter may be used: as a topping on bread products, topping for other food products such as waffles, pancakes, ice cream or other desserts, or as a sweetener in home cooking and/or in commercial food products, for example, filling for chocolates and other confections.

DEFINITIONS

"About" when used herein in relation to Brix measurement means ±2 units of measure, when used in relation to % sugar concentration, % air, % viscosity or % stablizer means ±20%, when used in relation to % enzyme treated maple syrup, % maple syrup, % untreated maple syrup, ratio of enzyme treated maple syrup to untreated maple syrup and % stabilizer means ±10%.

"Brix" when used herein means the refractometric sucrose value determined in accordance with the 'International Scale of Refractive Indices of Sucrose Solutions' and to which the applicable corrections for temperature and other solids have been made. The Brix value would be determined in accordance with the refractometric method outlined in the 'Official Methods of Analysis of the Association of Analytical Chemists'. In the case of maple syrup, the Brix value, as measured by refractometer or hydrometer, essentially equals the amount of sugar present because most (about 98%) of the solids are sugars.

"Crystallization" when used describing the shelf stable spreadable maple syrup product with the consistency of clear honey or the shelf stable, pourable, thick maple syrup describes crystals that are visible.

"Enzyme treated maple syrup" when used herein means maple syrup that has been treated with a sucrose cleaving enzyme.

"Maple-based product" when used herein means a product that contains maple syrup or maple sap.

"Maple butter" when used herein means the creamy smooth textured product obtained by the rapid cooling of a supersaturated maple syrup solution under high amounts of agitation. Maple butter is also known as maple cream. It is a crystallized product wherein the crystals are sufficiently small that they are not detectable by the human tongue or visible by the human eye without the aid of magnification.

"Maple syrup" when used herein means the concentrated or unconcentrated sap of trees of the botanical genus Acer.

"Pourable" when used herein means having a viscosity such that the product flows from a vessel, similar to table syrup.

"Pure maple-based product" when used herein means a maple-based product that contains only maple syrup, enzyme treated maple syrup or a blend of enzyme treated maple syrup and untreated maple syrup.

"Separation" when used to describe the maple butter means the formation of two or more distinct layers within the product.

"Shelf stable" when used herein in reference to the maple syrup product with the consistency of clear honey means that the maple syrup product is substantially free from crystallization for a period of at least 3 months. "Shelf stable" when used herein in reference to a maple butter product means that the maple butter is substantially free from separation for a period of at least 1 month.

"Spreadable" when used herein means distributable over a surface, in a manner similar to clear honey or churned honey.

"Stabilizer" when used herein means a substance that when added to a food product, inhibits crystallization, or prevents phase separation, or both.

A "sucrose-cleaving enzyme" is a hydrolysis enzyme which preferentially cleaves the beta-D-fructofuranoside linkage between the glucose and fructose molecules that make up sucrose.

"Untreated maple syrup" when used herein means maple syrup that has not been treated with a sucrose cleaving enzyme.

"Visible" when used herein means visible to the human eye without the use of magnification.

To make the high viscosity maple syrup of the present invention, any grade of maple syrup may be used as the starting material. Preferably, the maple syrup is high grade. The maple syrup is placed in a sanitary vessel such as a sterile agitated incubation tank and may optionally be diluted in order to optimize reaction conditions. Preferably, the maple syrup is diluted using sterile deionized water to a final Brix content of between about 55–66 degrees. Alternatively, maple sap which has been concentrated to about a final Brix content of only 55 and 66 degrees may be used in place of maple syrup.

An enzyme which cleaves sucrose into glucose and fructose is added to the maple syrup. Preferably an invertase enzyme is used. There are two main groups of invertase enzymes: 1) alpha-glucosidases which are also known as maltase, glucoinvertase, glucosidosucrase, maltase-glucoamylase, lysosomal alpha glucosidase, and acid maltase and 2) beta fructofuranosidases which are also known as invertase, saccharase and beta-fructosidase. Invertase is available commercially from Sigma Chemicals (Grade V: Practical from baker's yeast) and is used in the baking industry to control the amount of surface browning in bread and cookies. Invertase is added in the amount of 0.05% of the final weight of the diluted mixture. Invertase is sucrose specific and self-terminating in that once all of the substrate sucrose is cleaved, nothing else will be hydrolyzed.

The solution may be adjusted to the optimal pH for invertase pH 4.6 through known pH adjustment methods. Preferably, to maximize the natural maple flavor, the pH is not adjusted and the reaction still proceeds at the natural pH of maple syrup (pH 6.8). The time necessary to complete the hydrolysis of sucrose to glucose and fructose increases with increasing pH. At pH 6.8, conversion takes approximately 7 days.

The incubation temperature is preferably between 15 and 35 degrees Celsius and most preferably, the incubation should take place at room temperature (20–23 degrees Celsius) under continuous gentle agitation. Because of the low Brix, sanitary practices should be used when sampling and in further processing due to the potential for microbial growth.

The cleavage of sucrose to glucose and fructose can be monitored using various known methods. The preferred method is monitoring the optical rotation of the sugars. As the hydrolysis progresses, the muta-rotation decreases, and is negative when complete. A second method encompasses monitoring the hydrolysis using HPLC techniques methods (AOAC Official Method 977.20, Separation of Sugars in Honey). Glucose, fructose and sucrose can be separated by a carbohydrate column (Waters Inc., carbohydrate analysis column, part no. 84038) using a mobile phase of 83:17 acetonitrile: water. With corresponding standards, the three sugars can be identified and quantified. Hydrolysis is deemed complete after negligible amounts of sucrose are detectable.

Once the reaction is complete, preferably, the invertase enzyme is removed from the mixture or inactivated. The advantages of removing the enzyme from the syrup are to remove the visible haze and to remove the protein source which could initiate the Maillard browning reaction upon heating in the evaporation step. The Maillard reaction potentially creates bitter flavors, which would be objectionable in this product.

The enzyme can be removed by known means, including precipitation, hydrolysis and filtration. Preferably, the invertase is removed by filtration or can be inactivated by known means such as heating (>90 degrees Celsius) through a filter of pore size of less than 1 Tm.

It is also within the scope of this invention that the enzyme be inunobilized onto a resin bead that is then placed into a reaction column. The maple syrup is flushed through the column on a continuous basis, allowing the reaction to occur as the maple syrup passes over the resin beads onto which the enzyme had been attached. In such a case, the enzyme does not have to be removed through alternate means such as filtration as it remains bound to the resin beads in the column.

Once the enzyme is removed, the syrup can be concentrated to any concentration, depending on the viscosity that is desired in the product. It is preferably concentrated to between 72 and 90 degrees Brix, and most preferably to between 83 and 86 degrees Brix. This may be accomplished using known methods such as heating in an open kettle, vacuum pan evaporators and rising film or falling film evaporators. Concentration of the syrup is most preferably accomplished by heating the syrup to high temperature for short periods of time and flashing off the appropriate quantities of water to reach the desired Brix level. Low temperatures for longer periods of time with vacuum can also be used. Low temperature long time concentration is best carried out between 50 and 80 degrees Celsius, more preferably from 50 to 65 degrees Celsius and most preferably at 65 degrees Celsius and under vacuum (about 0.8 bar). The high viscosity syrup product produced in this manner may then be used by a consumer after the usual packaging steps, or it may be packaged and provided to the consumer. Maple butter, for example, may be produced by this method, however it is within the scope of the invention that products other than maple butter can also be produced in this manner. The concentrated or unconcentrated enzyme-treated maple syrup product can also be used to stabilize maple-based products or other products, by adding it to the other products.

To further improve the flavor profile, the dilute enzyme treated syrup is preferably blended with maple syrup of any grade prior to concentration. Optimum blends are 50:50, 55:45 and 60:40 (enzyme treated to non-enzyme treated syrup). The blended syrup can then be concentrated as described above. The maple flavor profile can be tailored to suit the retail climate by using different grades of maple syrup with varying flavor profiles in the incubation step and the blending step. The color of the final product can be controlled in a similar manner.

To make the shelf stable maple-based product of the present invention, for example maple butter, any grade of maple syrup may be used as the starting material. Preferably, the maple syrup is high grade. The maple syrup is combined with either (1) a small quantity of viscosity altering hydrocolloid stabilizer, preferably 0.1% carageenan or 0.1% xanthan, which has been first dispersed in a small quantity of water, or (2) enzyme treated maple syrup, preferably in a blend ratio of 20 to 25% enzyme treated maple syrup to 75 to 80% untreated maple syrup, or (3) one or more viscosity altering hydrocolloid stabilizers and enzyme treated maple syrup. The enzyme treated maple syrup is produced by adding enzyme to maple syrup and incubating the maple syrup.

The resultant blend is then concentrated, preferably to a concentration of between 83 and 87 degrees Brix, and most preferably to a concentration of 86 degrees Brix. This concentration may be accomplished using known methods such as heating in an open kettle and vacuum pan evaporation. Concentration of the resultant blend is most preferably accomplished by heating the syrup to high temperature for short periods of time in a plate heat exchanger, followed by flashing off the appropriate amounts of water to obtain the desired Brix content. The hot concentrated product is then transferred to a scraped surface heat exchanger where it is cooled rapidly under high amounts of agitation. The maple butter produced in this manner may then be provided to the consumer. The maple butter flavor profile can be tailored to suit the retail climate by using different grades of maple syrup with varying flavor profiles in the blending step. The color of the final product can be controlled in a similar manner.

To further improve the flavor profile of the maple-based product, for example, maple butter, air or an inert gas, for example nitrogen, can be whipped into the 84 degree Brix concentrated blend of maple syrup, enzyme treated maple syrup and/or hydrocolloid stabilizer, while cooling under high or rapid agitation. Preferably, a blend of pure maple syrup and enzyme treated maple syrup with a sugar ratio of 75 to 25 (pure maple syrup: enzyme treated maple syrup) is concentrated to 84 degrees Brix. Optionally, 0.15 xanthan can be added to the blend prior to concentration. After concentration, and during cooling, air can be whipped into the product to a final concentration of 1% to 15%, preferably between 9% to 12% air, most preferably to a final concentration of 120 air.

The present invention is described in more detail by reference to the following specific examples which are not to be construed as limiting.

EXAMPLE 1

Addition of Invert Sugar to Maple Syrup

The first stabilization technique evaluated was simple addition of invert sugar (glucose and fructose) to maple syrup and then concentrating to 82 degrees Brix on a hot plate. Four different levels of invert sugar were added: 1, 6, 10, and 20 percent. Crystallization was evident in all samples within three weeks of storage at room temperature. Interestingly, the more invert sugar added, the longer the time before crystallization was evident. However, with increasing invert sugar content, the maple flavor decreased substantially. The type of invert sugars was also evaluated. Three different invert sugars, solid invert, medium invert and high fructose corn syrup, were added at 20 percent of the total volume to 66 degrees Brix maple syrup and concentrated to 80 to 82 degrees Brix. Crystallization appeared in each of the samples within about three weeks.

EXAMPLE 2

Addition of Cream of Tartar to Maple Syrup

Cream of tartar (L-Tartaric Acid, Sigma Chemicals, Oakville, ON, Canada.) is an accepted way of converting sucrose to glucose and fructose (North American Maple Producers Manual s.7). Three levels of tartaric acid were evaluated: 0.02, 0.08 and 0.10 percent. Tartaric acid was added to the 66 degrees Brix maple syrup. The solution was heated to boiling, as it was thought that the heat added in concentrating the syrup to 80–82 degrees Brix was thought to be sufficient to cleave a portion of the sucrose to glucose and fructose. However, the resultant samples were very bitter in taste and had a distinct hazy appearance. All samples also crystallized after a two-day period at room temperature.

EXAMPLE 3

Enzymatic Cleavage of Sucrose to Glucose and Fructose with pH Adjustment

The enzyme invertase (Sigma Chemicals, Oakvill ON, Canada) was used to cleave sucrose to glucose and fructose. The optimal pH for this specific invertase enzyme is 4.5. However, the natural pH of maple syrup is 6.8. the first trial, 1 kg of maple syrup was placed in a sterile container. The pH of the maple syrup was adjusted to 5.0 using tartaric acid, closer to the optimal pH of the enzyme. To this, enzyme was added (1 g enzyme per 500 g syrup). In order to assist in the dispersion of the enzyme, the maple syrup was diluted to 55 degrees Brix using sterile deionized water. The solution was divided into two portions with one portion incubated at room tempera re (22 to 23 degrees Celsius) and the other was incubated at 33 degrees Celsius. After 6 day incubation period the sucrose, glucose and fructose content was determined using HPLC methods (AOAC Official Method 977.20, Separation of Sugars in Honey). At both temperatures, all of the sucrose had been converted to glucose and fructose A filtration step was then carried out to remove the enzyme (Whatman No. 42, Slow, Fine Crystalline Material; Fisher Canada, Nepean ON, Canada). The syrup was laced in a beaker atop a hot plate and heated to boiling. Concentration of this syrup to 82 Brix resulted in a product that was substantially free of crystals, and was shelf stable at room temperature for at least 2 months.

EXAMPLE 4

Enzymatic Cleavage of Sucrose to Glucose and Fructose without pH Adjustment

In an effort to reduce the effect of pH adjustment on the flavor of the product, the activity of the enzyme invertase was evaluated in maple syrup at the normal pH of maple syrup (pH 6.8) as described in Example 3. The incubation was carried out at room temperature, and allowed to proceed for 11 days. HPLC analysis of the sample showed that all of the sucrose had been converted to glucose and fructose. After filtration and concentrating to 82 degrees Brix, the resultant syrup had improved flavor and clarity. However, a more intense maple flavor may be desired. The flavor can be improved by using a more continuous evaporation/concentration system such as a plate heat exchanger with a flash system.

EXAMPLE 5

Flavor Improvements by Blending

To increase the maple flavor profile of the maple syrup at higher Brix, treated syrup (as described in Example 4) was blended with untreated maple syrup. Four blend ratios have been evaluated: 45:55, 50:50, 55:45, 60:40 ( ratio of enzyme treated maple syrup to untreated maple syrup). The concentration to 82 degrees Brix was carried out under vacuum (0.8 bar) and at a lower temperature (60 degrees Celsius). The resultant flavor profile was much improved over product produced in examples 3 and 4. Also, a shelf-life of more than 8 months is attainable with the 55:45 enzyme treated to pure maple syrup blend. Other blend ratios may be possible, for example 20 percent, but this would result in a shelf life of only about three weeks. For extended shelf life, a pure (100 percent) treated syrup could be concentrated as in Example 4, but the flavor and texture would be less desirable.

EXAMPLE 6

Shelf Life of Maple-Based Product at 75, 80, 83 and 87 Degrees Brix

Using a blend of 55:45 enzyme treated to non-enzyme treated syrup, further shelf life evaluations were carried out; evaluating the influence of maple syrup concentration. A blend of 55:45 enzyme treated to non enzyme treated syrup was concentrated using an experimental continuous evaporation system. The system was set-up to concentrate the product to 87 degrees Brix. A portion of this product was then diluted using deionized water to 75, 80 and 83 degrees Brix. Resultant samples were stored in the dark at room temperature (20–25 degrees Celsius). Shelf life studies of the four samples (75, 80, 83, 87 degrees Brix) show no visual signs of crystallization.

EXAMPLE 7

Viscosity

Figure 2:
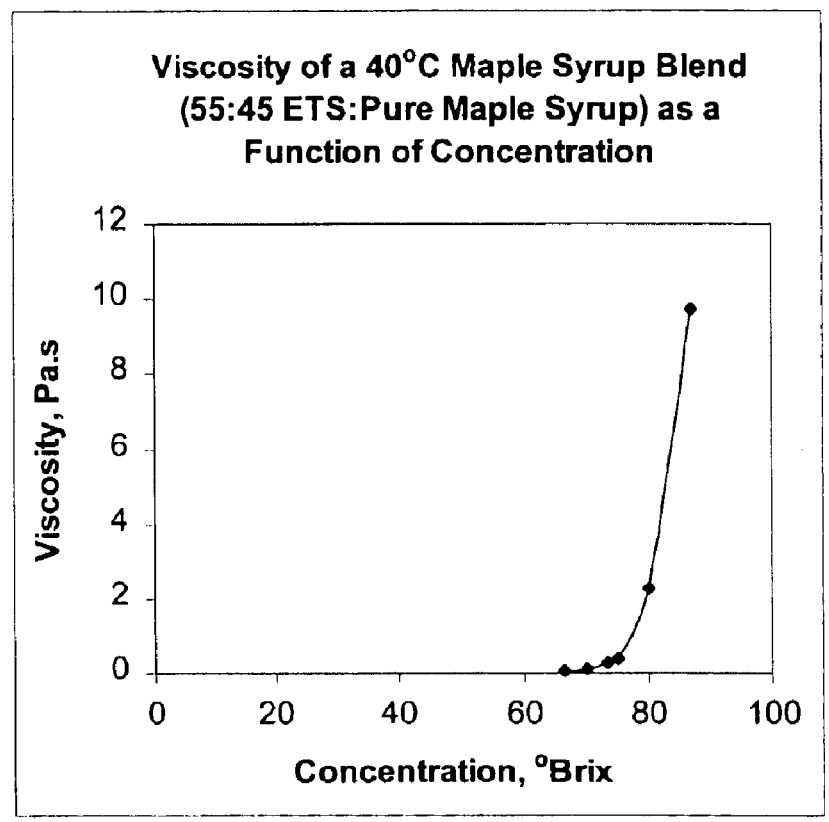
FIG. 2 is a graph showing the viscosity profile of a 55:45 enzyme treated to non-treated blend of maple syrup at various concentrations at 40° C.

The viscosity of the maple syrup was determined at various concentrations. A 55:45 enzyme treated to non enzyme treated syrup blend was concentrated to 87 degrees Brix using an experimental continuous evaporation system. A sample of this product was then diluted to 75, 80 and 83 degrees Brix. The viscosity of the maple syrup was measured at each of the seven concentrations (66.5, 70, 73.5, 75, 80, 83, 87 degrees Brix) on a Carri-Med $CLS^2$ 500 Rheometer (TA instruments, New Castle, Del.). A shear rate sweep (0 to 643 reciprocal seconds) was performed on each of the samples using a 2 cm, 4 degree cone and plate geometry. Temperature of the sample was controlled to 25 and 40 degrees Celsius. Because of the high viscosity of the samples, all samples were pre-warmed to 80 degrees Celsius prior to testing. Samples were then placed onto the testing apparatus and allowed to cool to the test temperature. The average viscosity of three runs is presented in Table 1 and shown in FIG. 1. The average viscosity at 40° C. is presented in Table 2 and shown in FIG. 2.

TABLE 1

Viscosity of Maple Syrup at Various Concentrations determined at 40 Reciprocal Seconds 25° C.

| Concentration | Viscosity, Pa · s |
|---|---|
| 75 | 1.48 |
| 80 | 11.8 |
| 83 | 61.5 |
| 87 | 487 |

TABLE 2

Viscosity of a 40° C. Maple Syrup Blend (55:45 ETS:Pure Maple Syrup) as a Function of Concentration

| Concentration | Viscosity |
|---|---|
| 66.5 | 0.05868 |
| 70 | 0.1145 |
| 73.5 | 0.262 |
| 75 | 0.3799 |
| 80 | 2.266 |
| 87 | 9.754 |

EXAMPLE 8

Maple Butter Containing Stabilizers

To test the efficacy of two stabilizers, a small-scale scraped surface heat exchanger (Sweden, Soft Serve Ice Cream Maker) was used to cool concentrated maple syrup solutions (86 degrees Brix) under high amounts of agitation. The following stabilizer levels of each stabilizer were evaluated: carageenan 0.05, 0.1 and 0.5 percent; xanthan 0.05, 0.1 and 0.33 percent. The stabilizer was first dispersed in a small quantity of water which was then blended with the unconcentrated maple syrup. Concentration to 86 degrees Brix was carried out in an open vat heated by steam. The hot concentrated product was then transferred into sealed containers that were subsequently cooled quiescently to 4 degrees Celsius. The cooled product was then poured into the scraped surface heat exchanger and agitated for 6 minutes. Product was drawn off the machine into 500 mL clear plastic containers. Samples from each stabilizer type and from each stabilizer concentration were monitored for stability as a function of time. All samples performed well, with limited amounts of separation being observed. The samples containing 0.1 percent carageenan did not show any signs of separation for 14 months. Similarly, the samples containing 0.1 percent xanthan also showed no signs of separation at 14 months.

EXAMPLE 9

Shelf Stable Maple-Based Products Using Enzyme Treated Maple Syrup

Enzyme treated maple syrup was produced by enzyme-treating maple syrup in the manner described in Example 3. This enzyme treated maple syrup was added to untreated maple syrup to produce maple butter. Blends of ratios of maple syrup with enzyme treated maple syrup were evaluated to test the stabilization effect of enzyme treated maple syrup to maple butter. The two blend ratios used in this experiment were 20% enzyme treated maple syrup to 80% maple syrup, and 25% enzyme treated maple syrup to 75% maple syrup. The resultant blends were concentrated to 86 degrees Brix and cooled rapidly under high agitation. A very smooth creamy maple butter product was obtained in both 20 and 25 percent enzyme treated maple syrup to maple syrup blends. Both products did not shown any signs of separation for 12 months.

EXAMPLE 10

Maple Butter with Air or Inert Gas and Enzyme Treated Maple Syrup

A sensory evaluation of maple butter made in example 9 indicated that the sugar intensity could be considered too strong for some people. Also, the product was somewhat difficult to spread. To increase product spreadability and to create a more appealing flavor profile, maple butter was made by concentrating to only 84 degrees Brix and whipping air into the product while cooling. To aid in the retention of the air and with the spreadability, 0.01 percent xanthan was also added to the blend before concentration. Five different amounts of air were incorporated into the maple butter after crystallizing (rapid cooling with agitation), corresponding to 9, 15, 26, 35 and 37 percent over-run in the sample.

Stability of products varied with the amount of air incorporated into the product. Air bubble destabilization (bubble growth) was visible after about 1 week of storage at room temperature for samples containing more than 15 percent air. Samples containing more than 15 percent air also exhibited phase separation after approximately 3 weeks of storage at room temperature.

Maple syrup product, containing 25 percent enzyme treated maple syrup, 75 percent maple syrup and 0.01 percent xanthan was concentrated to 85 degrees Brix. When 12 percent air was added in the rapid cooling and agitation process, air bubble destabilization was minimal, and phase separation was not detected, after 3 months of storage at room temperature. Optionally, inert gas, for example nitrogen, may be used.

While the invention has been particularly shown and described with a reference to a preferred embodiment, it will be understood by those skilled in the art that various changes in form and detail may be made therein without departing from the spirit and scope of the invention.

What is claimed is:

1. A method of stabilizing a pure maple-based product, comprising combining untreated maple syrup with a sucrose-cleaving enzyme treated maple syrup, in a ratio suitable for forming a stabilized, pure maple-based product.

2. The method of claim 1 which further comprises the step of concentrating the combined untreated maple syrup and sucrose-cleaving enzyme treated maple syrup to form the stabilized, pure, maple-based product.

3. The method of claim 1 wherein the sucrose-cleaving enzyme treated maple syrup is made according to a method comprising the steps of: (a) adding a sucrose-cleaving enzyme to a maple syrup; and (b) incubating the maple syrup to produce the sucrose-cleaving enzyme treated maple syrup.

4. A stabilized, pure maple-based product made by the method of claim 1.

5. A method of producing a shelf stable pure maple butter, comprising: (a) combining a maple syrup with a sucrose-cleaving enzyme treated maple syrup in a ratio suitable for forming a shelf stable maple butter; and (b) concentrating the product of step (a) to form pure shelf table maple butter.

6. The method of claim 5 wherein the sucrose-cleaving enzyme treated maple syrup is made according to a method comprising the steps of: (a) adding a sucrose-cleaving enzyme to a maple syrup; and (b) incubating the maple syrup to produce the sucrose-cleaving enzyme treated maple syrup.

7. The method of claim 5 wherein the ratio of sucrose-cleaving enzyme treated maple syrup to maple syrup is from about 20:80 to 25:75 by percentage of sugars present.

8. A method of producing a shelf stable maple butter, comprising: (a) adding a sucrose-cleaving enzyme to a maple syrup; (b) incubating the maple syrup to produce an enzyme treated maple syrup; (c) inactivating or removing the sucrose cleaving enzyme and (d) concentrating the enzyme treated maple syrup to produce the shelf stable maple butter.

9. The method of claim 8 wherein the sucrose-cleaving enzyme is invertase.

10. The method of claim 8 which comprises the additional step of diluting the maple syrup to about 55 to 66 degrees Brix prior to the step of adding the sucrose cleaving enzyme.

11. The method of claim 8 wherein the sucrose-cleaving enzyme is removed by filtration.

12. The method of claim 8 wherein the sucrose-cleaving enzyme is inactivated by heat treatment.

13. The method of claim 8 which comprises the additional step of monitoring the ratio of sucrose to fructose and glucose during step (b), and conducting step (c) at a predetermined sucrose to fructose and glucose ratio.

14. A maple butter made by the method of claim 5 or 8.

15. The method of using a sucrose-cleaving enzyme treated maple syrup as an ingredient in pure maple-based products, which comprises adding the sucrose cleaving enzyme treated maple syrup to pure maple product during manufacture of the pure maple-based product in an amount sufficient to stabilize the pure maple-based product.

16. A method of producing a shelf stable pure maple based product, the method comprising:
(a) adding a sucrose-cleaving enzyme to a maple syrup;
(b) incubating the maple syrup to produce the enzyme treated maple syrup;
(c) adding the enzyme treated maple syrup to a maple base product in a ratio suitable for forming a shelf-stable pure maple-based product; and
(d) concentrating the product of step (c) to produce the shelf stable pure maple based product.

17. The method of claim 16 which further comprise the step of removing or inactivating the sucrose-cleaving enzyme prior to the step of concentrating.

18. The method of claim 16 wherein the sucrose-cleaving enzyme is invertase.

19. The method of claim 17 wherein the sucrose-cleaving enzyme is removed by filtration.

20. The method of claim 17 wherein the sucrose-cleaving enzyme is inactivated by heat treatment.

21. The method of claim 17 which comprises the additional step of monitoring the ratio of sucrose to fructose and glucose during step (b) and removing or inactivating the sucrose-cleaving enzyme at a predetermined sucrose to fructose and glucose ratio.

22. The method of claim 16 wherein the product of step (c) is concentrated to a Brix level of between about 72 degrees Brix and about 90 degrees Brix.

23. The method of claim 16, wherein the maple syrup product is concentrated to between about 83 and about 87 degrees Brix.

24. The method of claim 16, wherein the maple syrup product is concentrated by a method selected from the group consisting of flash evaporation and under vacuum using low heat of between about 50 and about 65 degrees Celsius.

25. The method of claim 5 wherein the maple syrup solution is concentrated to between about 83 degrees Brix and 87 degrees Brix.

26. The method of using the product of claim 4 as a spread, sweetener or topping which comprises adding the product to food.

27. The method of claim 1 wherein the ratio of sucrose-cleaving enzyme treated maple syrup to untreated maple syrup is between about 20:80 and 25:75 by percentage of sugars present.

28. The method of claim 1 wherein the pure, stabilized maple-base product contains a ratio of glucose and fructose to sucrose, of between about 20:80 to 25:75 by percentage of sugars present.

29. The method of claim 3 which comprises the additional step of diluting the maple syrup to about 55 to 66 degrees Brix prior to step (a).

30. The method of claim 3 which further comprises the step of removing or inactivating the sucrose-cleaving enzyme prior to combining the untreated maple syrup with the sucrose-cleaving enzyme treated maple syrup.

31. The method of claim 6 which further comprises the step of removing or inactivating the sucrose-cleaving enzyme prior to combining the maple syrup with the sucrose-cleaving enzyme treated maple syrup.

32. The method of claim 31 wherein the sucrose-cleaving enzyme is removed by filtration.

33. The method of claim 31 wherein the sucrose-cleaving enzyme is inactivated by heat treatment.

34. The method of claim 6 which comprises the additional step of diluting the maple syrup to about 55 to 66 degrees Brix prior to the step of adding the sucrose cleaving enzyme.

35. The method of claim 5 wherein the shelf stable pure maple butter contains a ratio of glucose and fructose to sucrose of between about 20:80 to 25:75 by percentage of sugars present.

36. The method of claim 13 wherein the predetermined ratio of sucrose to fructose and glucose is between about 75:25 to 80:20 by percentage of sugars present.

37. The method of claim 16 wherein the ratio of enzyme treated maple syrup to maple-based product is between about 20:80 to 25:75 by percentage of sugars present.

38. The method of claim 16 wherein the shelf stable pure maple-based product contains a ratio of glucose and fructose to sucrose of between about 20:80 to 25:75 by percentage of sugars present.

39. The method of claim 16 which comprises the additional step of diluting the maple syrup to about 55 to 66 degrees Brix prior to the step of adding the sucrose cleaving enzyme.

40. The method of claim 8 wherein the enzyme treated maple is concentrated to between about 83 degrees Brix and 86 degrees Brix.

41. The method of claim 29 wherein the sucrose-cleaving enzyme is removed by filtration.

42. The method of claim 29 wherein the sucrose-cleaving enzyme is inactivated by heat treatment.

43. The method of claim 30 which comprise the additional step of monitoring the ratio of sucrose to fructose and glucose during step (b) and removing or inactivating the sucrose-cleaving enzyme at a predetermined sucrose to fructose and glucose ratio.

* * * * *